US00PP19675P2

(12) United States Plant Patent
Van Spronsen

(10) Patent No.: US PP19,675 P2
(45) Date of Patent: Feb. 3, 2009

(54) ***CHRYSANTHEMUM* PLANT NAMED 'POWER BRONZE'**

(50) Latin Name: *Chrysanthemum×morifolium*
Varietal Denomination: Power Bronze

(75) Inventor: Simon Van Spronsen, Niagara on the Lake (CA)

(73) Assignee: Willy's Greenhouse Ltd., Niagara on the Lake, Ontario (CA)

( * ) Notice: Subject to any disclaimer, the term of this patent is extended or adjusted under 35 U.S.C. 154(b) by 0 days.

(21) Appl. No.: 12/011,936

(22) Filed: Jan. 30, 2008

(51) Int. Cl.
*A01H 5/00* (2006.01)

(52) U.S. Cl. ..... Plt./296
(58) Field of Classification Search ..... Plt./296
See application file for complete search history.

*Primary Examiner*—Annette H Para
(74) *Attorney, Agent, or Firm*—Penny J. Aguirre

(57) ABSTRACT

A new cultivar of *Chrysanthemum,* 'Power Bronze', characterized by it's early and free flowering habit, its daisy-type inflorescences with soft yellow colored ray florets that are diffused with red-purple to appear bronze and surround bright yellow disk florets, its vigorous freely branched growth habit, its dark green foliage and its uniform, rounded and outward spreading plant habit.

2 Drawing Sheets

Botanical classification: *Chrysanthemum×morifolium.*
Variety denomination: 'Power Bronze'.

BACKGROUND OF THE INVENTION

The present invention relates to a new and distinct cultivar of *chrysanthemum* plant botanically known as *Chrysanthemum×morifolium* 'Power Bronze'and hereinafter by its cultivar name, 'Power Bronze'.

The new *chrysanthemum* 'Power Bronze' was discovered by the inventor as a naturally occurring branch mutation of the *Chrysanthemum* cultivar 'Apricot Cherie' (U.S. Plant Pat. No. 12961) in July 2007 in Niagara on the Lake, Ontario, Canada.

Asexual reproduction of the new cultivar was first accomplished via stem cuttings in July 2007 in Niagara on the Lake, Ontario, Canada. The characteristics of this cultivar have been determined to be stable and are reproduced true to type in successive generations.

SUMMARY OF THE INVENTION

The following traits have been repeatedly observed and are determined to be the characteristics of the new cultivar of *Chrysanthemum.* These attributes in combination distinguish by 'Power Bronze' as unique from all other varieties of *Chrysanthemums* known to the inventor.

1. The inflorescences of 'Power Bronze' exhibit soft yellow colored ray florets that are diffused with red-purple to appear bronze and surround bright yellow disk florets.
2. The inflorescence buds of 'Power Bronze' are red-purple in color.
3. 'Power Bronze' is early flowering with daisy-type inflorescences about 4 cm in diameter.
4. 'Power Bronze' has a freely branched, uniform, rounded and outward plant habit.
5. 'Power Bronze' has a uniform flowering response.
6. 'Power Bronze' exhibits dark green foliage.
7. 'Power Bronze' is a vigorous grower.

The parent plant of 'Power Bronze', 'Apricot Cherie', differs from 'Power Bronze' in having soft pink to tan colored ray florets and inflorescent buds that are green in color. Based on its growth habit, flowering response and flower type, 'Power Bronze' can be most closely compared to, 'Bronze Cherie' which has grayed-orange colored ray florets, 'Honey Cherie' which has yellow ray florets overlaid with grayed-orange and 'Power Yellow' (U.S. Plant Pat. No. 18,175) which has yellow ray florets.

BRIEF DESCRIPTION OF THE DRAWINGS

The accompanying colored photographs illustrate the overall appearance and distinct characteristics of the new *Chrysanthemum,* 'Power Bronze'. The photographs were taken of a plant grown in a 5-inch pan pot planted with 3 rooted cuttings and grown under greenhouse conditions for 10 weeks.

Figure 1:
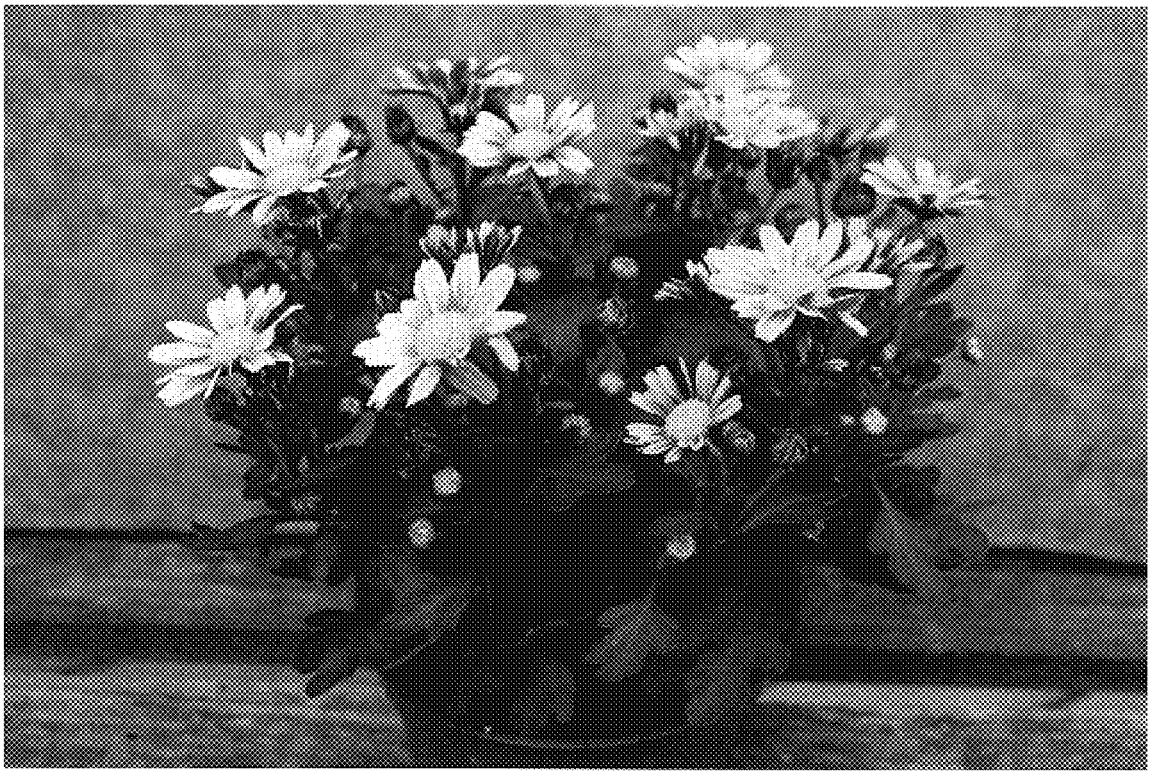
FIG. 1 is a photograph that provides a side perspective view of a typical plant in bloom when grown as a spray-type.
Figure 2:
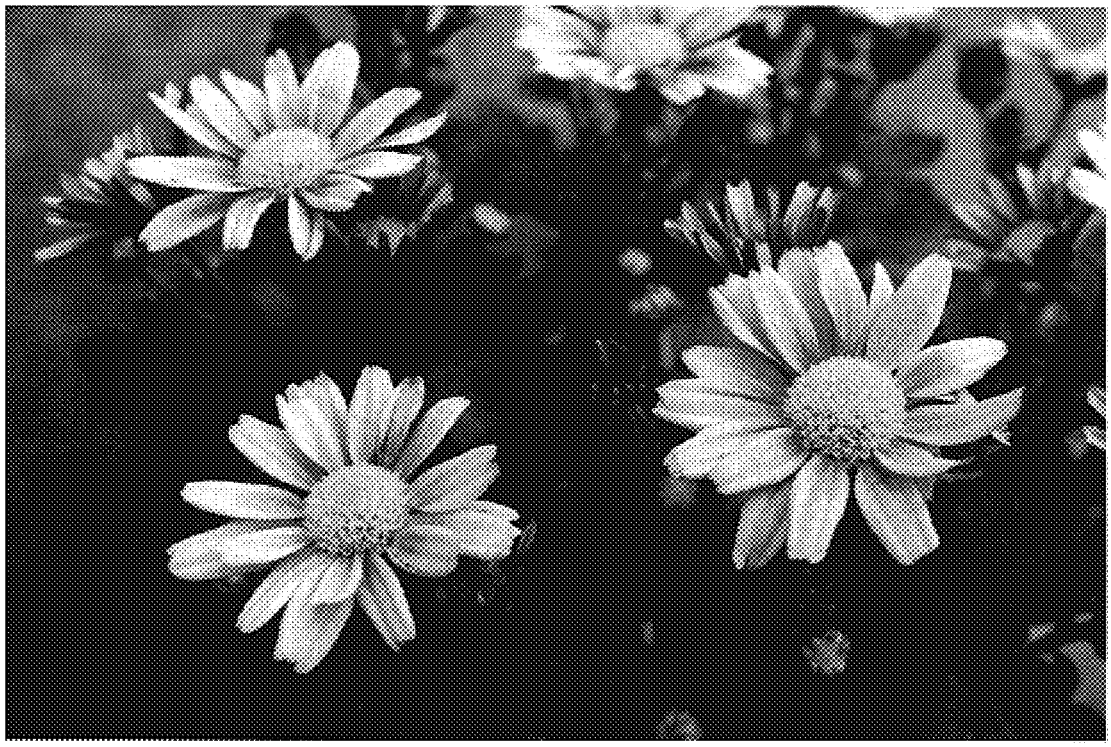

The photograph in FIG. 2 provides a close-up view of the inflorescences of 'Power Bronze'.

The colors in the photographs are as close as possible with the photographic and printing technology utilized. The color values cited in the detailed botanical description accurately describe the colors of the new *Chrysanthemum.*

DETAILED BOTANICAL DESCRIPTION

The following is a detailed description of plants of the new cultivar as grown in a 5-inch pan pot planted with 3 single pinched rooted cuttings and grown under greenhouse conditions at an average temperature of 65° F. for 10 weeks. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Commercial classification.*—Daisy-type potted *Chrysanthemum.*

*Flowering response.*—Early blooming, flowering occurs after short day treatment in about 52 days in spring, summer and fall and 56 days in winter.

*Plant type.*—Herbaceous, grown as a potted *Chrysanthemum* as a spray-type.

*Plant habit.*—Freely branched, uniform, outward plant habit with rounded crown.

*Height and spread.*—Reaches about 15 cm in height and 23 cm in width when grown under the conditions tested under greenhouse conditions.

*Diseases resistance.*—No susceptibility or resistance to diseases common to *Chrysanthemum* has been observed under commercial greenhouse productions.

*Root description.*—Fibrous.

Growth and Propagation:

*Propagation.*—Terminal stem cuttings.

*Time to root.*—About 8 days at 20° C.

*Production.*—Rooted cuttings grown on at 65° F. finish in a 5-inch pan pot in 8 weeks.

*Growth rate.*—Vigorous.

Stem description:

*Stem color.*—138B with pubescence of 138C.

*Stem strength.*—Strong and flexible.

*Stem surface.*—Pubescent

*Branching habit and quantity.*—Freely branched, about 4 branches per stem after removal of the apical meristem (pinching).

*Lateral branch size.*—About 11 cm in length and about 3.5 mm in width.

*Internode length.*—Lateral branches in a whorl from pinched node.

Foliage description:

*Leaf division.*—Simple.

*Leaf shape.*—Blade is broadly ovate with narrowing towards base.

*Leaf base.*—Blade base is cuneate, leaf base truncate.

*Leaf apex.*—Rounded to broadly acute and mucronate.

*Leaf margin.*—Matures to trifid to five-lobed with apex of lobes rounded with mucrunate tips.

*Leaf texture.*—Upper surface slightly pubescent, lower surface pubescent

*Leaf venation.*—Palmate, upper surface matches leaf color becoming 138C at base of midrib, lower surface 138C.

*Leaf attachment.*—Sessile.

*Leaf arrangement.*—Alternate.

*Leaf number.*—Average of 22 per lateral branch.

*Leaf internode length.*—Average of 9 mm.

*Leaf color.*—Young foliage; upper surface 137B, lower surface 191A with pubescence of 191B, mature foliage; upper surface 137A, lower surface 191A with pubescence of 191B.

*Leaf size* (*fully expanded*).—Average of 5.2 cm in length and 3.2 cm in width (expanded blade portion is an average of 3.8 cm in length).

*Fragrance of foliage.*—Fragrant if bruised.

Flower description:

General description:

*Inflorescence type.*—Composite, daisy form with oblong shaped ray florets and disk flowers arranged acropetally on a capitulum, inflorescences typically borne in compound corymbs.

*Postproduction longevity.*—Conditions dependent, inflorescences maintain good color and substance for about 2 weeks in an interior environment.

*Fragrance.*—Faint.

*Quantity of inflorescences.*—Average of 17 per lateral stem, about 155 per plant produced from 3 cuttings.

*Inflorescence size.*—About 8 mm in depth and 4 cm in diameter, diameter of disk about 1.2 cm.

*Inflorescence buds.*—About 1 cm in depth and 8 mm in diameter, globose becoming ovate in shape prior to opening, 60C to 60B in color with phyllaries 138A to 138B.

*Peduncle.*—Strong, flexible, held from upright to an angle of 30° to vertical, surface is pubescent, an average of 3 cm in length and 2 mm in width, 138A to 138B in color.

*Involucral bracts* (*phyllaries*).—Arranged in two layers, 138A to 138B in color with translucent margins, about 3 mm in length and 1.5 mm in width, surface is glandular with pubescence on margins.

*Receptacle.*—About 4 mm in diameter and 3 mm in depth, 144A to 144B in color.

Ray florets (capitulate):

*Number.*—Average of 21.

*Arrangement.*—In 2 rows.

*Shape.*—Elongated oblong.

*Aspect.*—Emerge vertical and open to primarily horizontal when fully open.

*Size.*—Average of 1.7 cm in length and 6 mm in width.

*Petal apex.*—Rounded with one or two notches.

*Petal base.*—Cuneate.

*Petal margins.*—Entire.

*Petal texture.*—Glabrous on upper and lower surface and ridged.

*Petal color.*—Opening and fully open, upper surface; 11A suffused towards base with 60C, opening lower surface; 11B heavily suffused with 59B, fully open lower surface 11B heavily suffused with 59C with margins 11B, base surrounding pistil 144D.

Disk Florets (perfect):

*Arrangement.*—Massed in center of receptacle.

*Quantity.*—Average of 72.

*Shape.*—Tubular.

*Size.*—About 5 mm in length and about 1.5 mm in width.

*Color.*—Immature 154B, mature 7A.

Reproductive organs:

*Presence.*—Disk flowers are perfect, ray flowers are carpellate.

*Gynoecium.*—1 Pistil per disk and ray floret, 3.5 mm in length, style color 154D, stigma color 7C.

*Androcoecium.*—5 stamens per disk floret, fused into tube surrounding style, anthers are translucent and color 154D, pollen is sparse in quantity and 17A in color.

*Seed.*—Seed production has not been observed under the conditions tested.

It is claimed:

1. A new and distinct cultivar of *Chrysanthemum* plant named 'Power Bronze' as herein illustrated and described.

* * * * *